US012642705B2

(12) United States Patent
Kanemaru et al.

(10) Patent No.: US 12,642,705 B2
(45) Date of Patent: Jun. 2, 2026

(54) DRESSING MATERIAL FOR PUNCTURE

(71) Applicants: Nichiban Co., Ltd., Tokyo (JP); The University of Tokyo, Tokyo (JP)

(72) Inventors: Tatsuya Kanemaru, Tokyo (JP); Kyohei Matsuo, Tokyo (JP); Subaru Matsuo, Tokyo (JP); Hiromi Sanada, Tokyo (JP); Ryoko Murayama, Tokyo (JP); Mari Abe, Tokyo (JP)

(73) Assignees: NICHIBAN CO., LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 138 days.

(21) Appl. No.: 18/724,721

(22) PCT Filed: Dec. 26, 2022

(86) PCT No.: PCT/JP2022/047986

§ 371 (c)(1),
(2) Date: Feb. 18, 2025

(87) PCT Pub. No.: WO2023/127821

PCT Pub. Date: Jul. 6, 2023

(65) Prior Publication Data

US 2025/0169994 A1      May 29, 2025

(30) Foreign Application Priority Data

Dec. 28, 2021      (JP) ................................. 2021-214959

(51) Int. Cl.
*A61F 13/0246* (2024.01)
*A61F 13/02* (2024.01)
(Continued)

(52) U.S. Cl.
CPC ...... *A61F 13/0256* (2013.01); *A61F 13/0253* (2013.01); *A61F 13/0266* (2013.01);
(Continued)

(58) Field of Classification Search
CPC .. A61F 2013/00412; A61F 2013/00706; A61F 2013/00846; A61F 13/0253;
(Continued)

(56) References Cited

U.S. PATENT DOCUMENTS

| | | | |
|---|---|---|---|
| 5,769,807 A * | 6/1998 | Haddock | A61F 13/023 |
| | | | 424/433 |
| 2013/0172843 A1* | 7/2013 | Kurata | A61F 13/15731 |
| | | | 156/60 |
| 2013/0289404 A1 | 10/2013 | Sloth et al. | |
| 2021/0038249 A1 | 2/2021 | Bendtsen et al. | |
| 2021/0177456 A1 | 6/2021 | Vo et al. | |

FOREIGN PATENT DOCUMENTS

| | | |
|---|---|---|
| JP | 61-228868 A | 10/1986 |
| JP | H10-33655 A | 2/1998 |

(Continued)

OTHER PUBLICATIONS

International Search Report for corresponding International Application No. PCT/JP2022/047986 mailed Mar. 28, 2023.
(Continued)

*Primary Examiner* — Keri J Nelson
(74) *Attorney, Agent, or Firm* — Chrisman Gallo Tochtrop LLC

(57) ABSTRACT

A dressing material for puncture of the present invention includes a support film, a frame sheet, and a release liner, which are laminated from an upper side in this order. An adhesive is used to bond the support film and the frame sheet, and bond the frame sheet and the release liner. The support film is a base material having a thickness of from 10 μm to 80 μm. The adhesive has a mass per unit area of from 30 g/m² to 80 g/m².

18 Claims, 7 Drawing Sheets

(51) Int. Cl.
*A61M 25/01* (2006.01)
*A61M 25/02* (2006.01)
*A61F 13/00* (2006.01)

(52) U.S. Cl.
CPC ............... *A61F 2013/00412* (2013.01); *A61F 2013/00706* (2013.01); *A61F 2013/00846* (2013.01); *A61M 25/0108* (2013.01); *A61M 2025/0273* (2013.01)

(58) Field of Classification Search
CPC ............ A61F 13/0256; A61F 13/0266; A61M 25/0108; A61M 25/02; A61M 2025/0273
See application file for complete search history.

(56) References Cited

FOREIGN PATENT DOCUMENTS

| | | |
|---|---|---|
| JP | 2009-017941 A | 1/2009 |
| JP | 2014-507181 A | 3/2014 |
| JP | 6176850 B2 | 8/2017 |
| JP | 2021-511946 A | 5/2021 |
| WO | 2016/031001 A1 | 3/2016 |

OTHER PUBLICATIONS

Written Opinion for corresponding International Application No. PCT/JP2022/047986 dated Mar. 28, 2023.

\* cited by examiner (A)

(B)

(A)

(B)

(C)

(A)

(B)

(C)

(D)

(E)

(A)

(B)

DRESSING MATERIAL FOR PUNCTURE

CROSS-REFERENCE TO RELATED APPLICATIONS

This application is a national stage entry of International Application No. PCT/JP2022/047986 filed on Dec. 26, 2022, which claims the benefit of priority to Japanese Application No. JP2021-214959, filed Dec. 28, 2021, the entire disclosures of which are hereby incorporated herein by reference.

TECHNICAL FIELD

The present invention relates to a dressing material for puncture that allows puncture by a puncture device, such as a catheter under ultrasound guidance, allows the puncture device to be directly and easily fixed, and further allows an observation of a holding state of a tip of the puncture device over time.

BACKGROUND ART

When a catheter is placed in a peripheral vein, improper puncture and fixation cause a complication, such as vein inflammation. In view of this, attempts have been made to standardize a technique (ultrasound-guided puncture) for placing a catheter while observing the state of a blood vessel and a puncture device with ultrasonic waves. However, puncturing a site applied with a jelly for ultrasound examination (hereinafter abbreviated as an ultrasonic jelly) raises concerns about clogging of a needle and an infection due to the ultrasonic jelly.

Currently, while ultrasonic examinations are performed by applying a disinfectant solution or the like instead of the ultrasonic jelly in some cases, there are difficulties in the examination and the standardization because the disinfectant solution is volatile.

Here, when the ultrasonic jelly is applied over a dressing material for puncture and an ultrasonic observation is performed through the dressing material for puncture, a puncture site body surface can be separated from the ultrasonic jelly. Therefore, it can be expected to avoid a pain and a complication due to puncture needle clogging and puncture failure, improve the accuracy of the technique, and avoid the infection. Furthermore, since the catheter can be easily fixed after the puncture, improved workability can be expected.

There is disclosed an instrument for aiding ultrasound-guided body surface puncture using a dressing material in ultrasound-guided puncture (Patent Document 1). However, specifications excellent in ultrasonic transparency (types and thicknesses of adhesive and base material) are not examined. While products manufactured by another company (UL-TRADRAPE™, Parker Laboratories Inc., Patent Document 2, Patent Document 3) similar to the product of the present invention have been developed, ultrasonic transparency is insufficient. Studies conducted so far have revealed that there are concerns about puncture failure due to the poor observation of anatomical structure, such as a blood vessel, propagation of bacteria in long-term application due to the low moisture permeability of the tape, and the like.

PRIOR ART DOCUMENTS

Patent Documents

Patent Document 1: WO 2016/031001
Patent Document 2: Japanese Patent No. 6176850
Patent Document 3: JP-T-2021-511946

DISCLOSURE OF THE INVENTION

Problems to be Solved by the Invention

As seen from the above-described circumstances, a dressing material for puncture that allows a puncture device to be placed and fixed under an ultrasound guidance is required to have an excellent ultrasonic transparency and a high moisture permeability.

The present invention provides a dressing material for puncture that allows puncture while observing an anatomical structure and a puncture device with an ultrasound examination device by using an ultrasonic jelly applied over an uppermost film after attaching the dressing material for puncture, allows the puncture device to be directly fixed, and further allows an observation of a holding state of a tip of the puncture device over time.

The present invention provides a dressing material for puncture that allows avoiding entering of air between an adhesive and a skin when the dressing material for puncture is attached, thereby improving an ultrasonic transparency and a moisture permeability.

Solutions to the Problems

The present inventors have seriously studied, and thus completed a dressing material for puncture having an appropriate viscoelasticity allowing a puncture device to be fixed, having a high moisture permeability, and further having an excellent ultrasonic transparency.

That is, the present invention relates to, as a first aspect, a dressing material for puncture that includes a support film, a frame sheet, and a release liner. The support film has an ultrasonic transparency. The frame sheet includes an observation window to observe a holding state of a tip of a puncture device fixed to a body surface. The support film, the frame sheet, and the release liner are laminated from an upper side in this order. An adhesive is used to bond the support film and the frame sheet, and bond the frame sheet and the release liner. The support film is a film base material having a thickness of from 10 μm to 80 μm. The adhesive has a mass per unit area of from 30 $g/m^2$ to 80 $g/m^2$.

The present invention relates to, as a second aspect, the dressing material for puncture described in the first aspect in which the adhesive that bonds the support film and the frame sheet is an acrylic adhesive or a urethane adhesive containing a copolymer where (meth)acrylic acid alkyl ester is a main component.

The present invention relates to, as a third aspect, the dressing material for puncture described in the first aspect or the second aspect in which in the adhesive that bonds the support film and the frame sheet has a storage elastic modulus of 15 KPa or less and a loss tangent (tan δ) of 0.4 or more at an angular frequency of 1 rad/s obtained by a dynamic viscoelasticity measurement at 32° C.

The present invention relates to, as a fourth aspect, the dressing material for puncture described in the first aspect or the second aspect in which in the adhesive that bonds the support film and the frame sheet has a storage elastic modulus of 28 KPa or less and a loss tangent (tan δ) of 0.65 or more at an angular frequency of 1 rad/s obtained by a dynamic viscoelasticity measurement at 32° C.

The present invention relates to, as a fifth aspect, the dressing material for puncture described in any one of the first aspect to the fourth aspect in which a base material used for the support film is polyethylene terephthalate, polyethylene, polyurethane, or oriented polypropylene.

The present invention relates to, as a sixth aspect, the dressing material for puncture described in any one of the first aspect to the fifth aspect in which a total thickness of the support film and an adhesive part filling a space of the observation window is from 47 μm to 120 μm.

The present invention relates to, as a seventh aspect, the dressing material for puncture described in any one of the first aspect to the sixth aspect in which a base material used for the frame sheet is a polyurethane nonwoven fabric or a polyethylene terephthalate nonwoven fabric.

The present invention relates to, as an eighth aspect, the dressing material for puncture described in any one of the first aspect to the seventh aspect in which the frame sheet further includes a slit portion to expose the puncture device.

The present invention relates to, as a ninth aspect, the dressing material for puncture described in any one of the first aspect to the eighth aspect further including a folded tape coupled with the release liner.

The present invention relates to, as a tenth aspect, the dressing material for puncture described in the ninth aspect in which the folded tape is provided to be coupled with the release liner at a part of a lower surface of the release liner to partially cover the observation window.

The present invention relates to, as an eleventh aspect, the dressing material for puncture described in the ninth aspect or the tenth aspect in which the release liner is provided with one cutout portion at each of both edges of the release liner in a longitudinal direction, and a side edge of the folded tape in an opposite side of a device placement side overlaps with a straight line connecting the two cutout portions in a short side direction.

The present invention relates to, as a twelfth aspect, the dressing material for puncture described in any one of the first aspect to the eleventh aspect further including a non-adhesive processed portion between the frame sheet and the release liner to avoid bonding the frame sheet and the release liner.

The present invention relates to, as a thirteenth aspect, the dressing material for puncture described in the twelfth aspect in which the non-adhesive processed portion is formed of a non-adhesive seal.

The present invention relates to, as a fourteenth aspect, the dressing material for puncture described in any one of the first aspect to the thirteenth aspect further including a carrier film directly in close contact with the support film on an upper side of the support film. The carrier film has a thickness of from 10 μm to 80 μm.

Effects of the Invention

The use of the dressing material for puncture of the present invention allows puncture while observing the ultrasound images of the anatomical structure, such as a blood vessel, and the puncture device without a touch of the ultrasonic jelly with the body surface or the puncture device, such as a catheter. Accordingly, the possibility of clogging of the puncture device and infections due to the ultrasonic jelly can be reduced, the puncture device can be easily fixed after the puncture, and the improvement of workability can be expected. Further, the holding state of the tip of the fixed puncture device can be confirmed through the observation window.

In addition, since the skin is a rough surface having skin ridges and skin grooves having a depth of about 20 to 40 μm, air enters between the adhesive and the skin in some cases when the dressing material for puncture is attached. In consideration of decrease in ultrasonic transparency to the skin through the dressing material for puncture due to the air entering, in the present invention, the application thickness and viscoelastic properties of the adhesive necessary for penetrating into the skin grooves to avoid the air entering are devised. As a result, by applying the adhesive having the appropriate viscoelastic properties and the high moisture permeability over a support body with the application thickness of 30 μm or more, discomfort during attachment and the infection risk are reduced, thereby allowing the attachment for a long period of time. Furthermore, the frequency of re-puncture for replacement of the puncture device due to failure of the puncture procedure, infection of the puncture site, and discomfort is reduced. The dressing material for puncture provides a remarkable effect leading to the improvement of the patient's QOL (quality of life) and reduction of the burden on medical workers.

BRIEF DESCRIPTION OF THE DRAWINGS

FIG. 1(A) is a plan view and FIG. 1(B) is a bottom view illustrating an example of a dressing material (1) for puncture of the present invention.

FIG. 5(A) illustrates the carrier film (10), FIG. 5(B) illustrates the support film (2), FIG. 5(C) illustrates the frame sheet (3), FIG. 5(D) illustrates the non-adhesive processed portion (non-adhesive seal) (11), FIG. 5(E) illustrates the release liner (4), and FIG. 5(F) illustrates a folded tape (7).

FIG. 6(A) is a dressing material for puncture in which the frame sheet is removed from the dressing material for puncture of FIG. 2. FIG. 6(B) is a dressing material for puncture further including the non-adhesive processed portion (11) between the support film (2) and the release liner (4) illustrated in FIG. 6(A). FIG. 6(C) is a dressing material for puncture further including a carrier film directly in close contact with the support film on an upper side of the bonded support film and release liner illustrated in FIG. 6(A).

FIG. 8(A) to FIG. 8(E) are ultrasonic photographs with ratings 0 to 4, respectively based on evaluation criteria of Table 2.

FIG. 9(A) is a photograph taking an image of a state in which a probe is pressed onto a surface over which an ultrasonic jelly is applied of a sample attached to a pad portion of Sakamoto model. FIG. 9(B) is an obtained ultrasonic image taking an image of a peripheral area of a blood vessel of Sakamoto model.

FIG. 1 to FIG. 6 are provided only for explanations, and do not necessarily illustrate an actual dressing material.

DESCRIPTION OF PREFERRED EMBODIMENTS

A puncture device of the present invention is, for example, a needle, a catheter, a cannula, or a guide wire, and used for puncturing a vein or an artery, or puncturing another anatomical structure. The anatomical structure includes, for example, a vein, an artery, a nerve, a tendon, a nerve sheath, a muscle, an adipose tissue, and the like.

A body surface of the present invention includes skin of human and animals, such as dogs, cats, cattle, and horses. (Structure of Dressing Material for Puncture)

The dressing material for puncture of the present invention is a flat patch material for medical treatment. FIG. 1(A) illustrates an example of a plan view of the dressing material for puncture of the present invention. FIG. 1(B) illustrates an example of a bottom view of the dressing material for puncture of the present invention. FIG. 2 is a cross-sectional view of the dressing material for puncture along the line A-A' illustrated in FIG. 1(A). A direction indicated by the arrow is a skin side.

Figure 1:
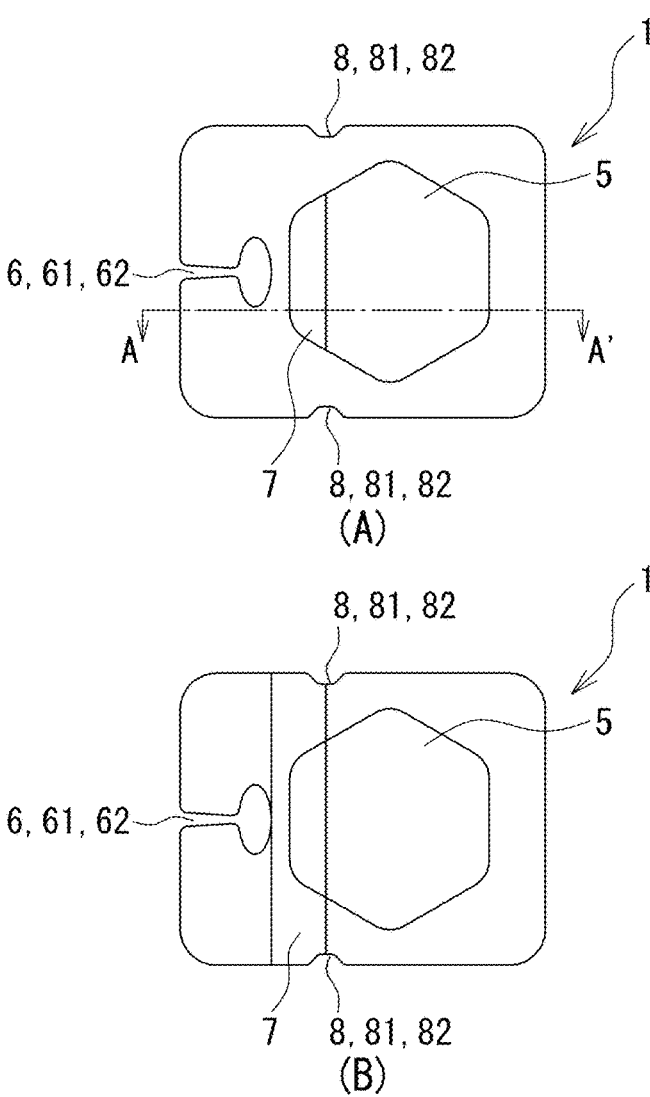
Figure 2:
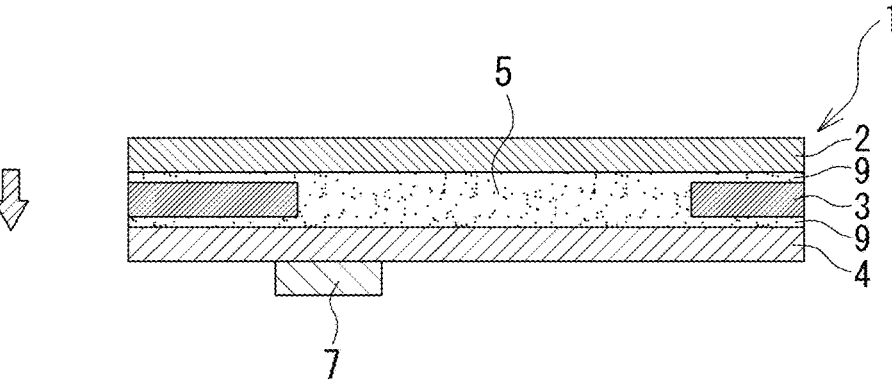
FIG. 2 is a cross-sectional view along the line A-A' of the dressing material (1) for puncture illustrated in FIG. 1(A). An arrow direction indicates a side adhered to a body surface.

While FIG. 1 illustrates a rectangular dressing material for puncture, the shape of the dressing material for puncture can be freely changed as necessary.

One embodiment of the dressing material for puncture of the present invention is configured by laminating layers as illustrated in the cross-sectional view of FIG. 2. In the order from the upper side, a support film (2) having an ultrasonic transparency, a frame sheet (3) provided with an observation window (5) to observe a holding state of a tip of a puncture device fixed to a body surface, and a release liner (4) are laminated. The support film (2) is bonded to the frame sheet (3) by an adhesive (9), and the frame sheet (3) is bonded to the release liner (4) by the adhesive (9). The observation window (5) between the release liner (4) and the support film (2) is filled with the adhesive (9).

Basically, the dressing material is attached to locate the tip of a puncture device (12) inserted into a body (see FIG. 7) at about the center of the dressing material. A portion of the puncture device placed outside the body is fixed by a peripheral portion of the dressing material. The portion of the dressing material at which the puncture device placed outside is located is referred to as a device placement side of the dressing material in the present invention.

Figure 3:
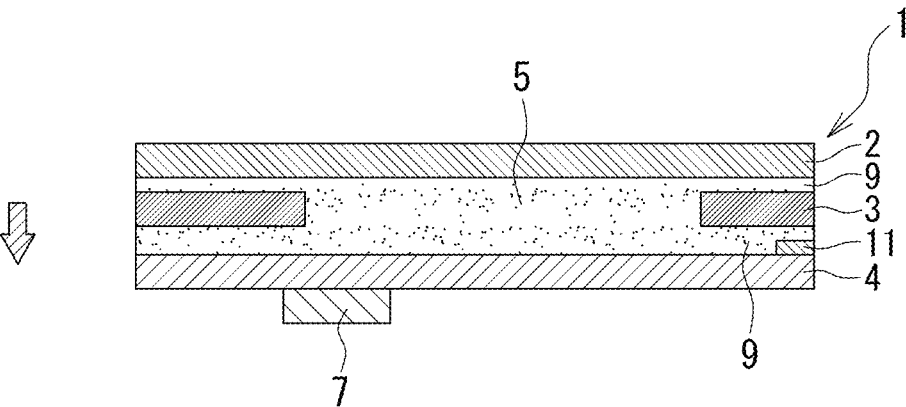
FIG. 3 is a cross-sectional view of a dressing material for puncture provided with a non-adhesive processed portion (11) between a frame sheet (3) and a release liner (4) in the dressing material for puncture illustrated in FIG. 2. An arrow direction indicates a side adhered to a body surface.
Figure 4:
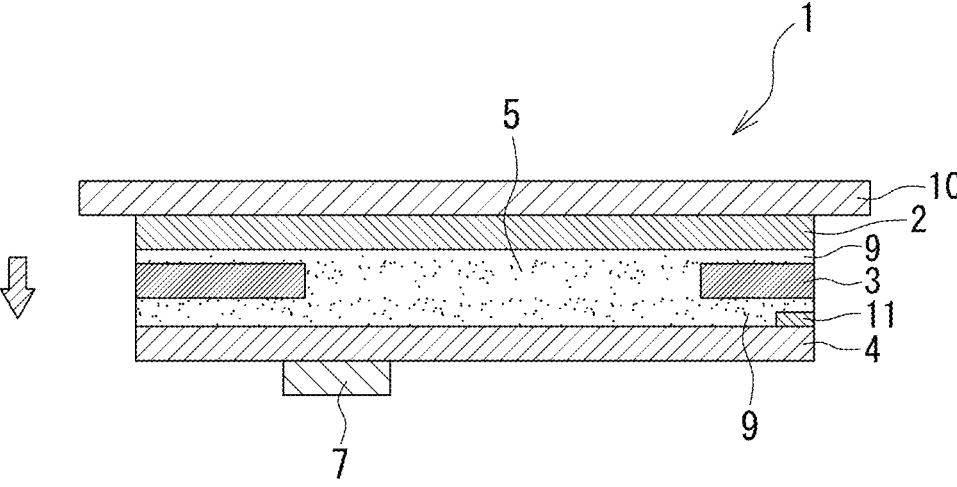
FIG. 4 is a cross-sectional view of an exemplary dressing material for puncture of the present invention further including a carrier film (10) directly in close contact on a support film (2) of the dressing material for puncture of FIG. 3.
Figure 5:
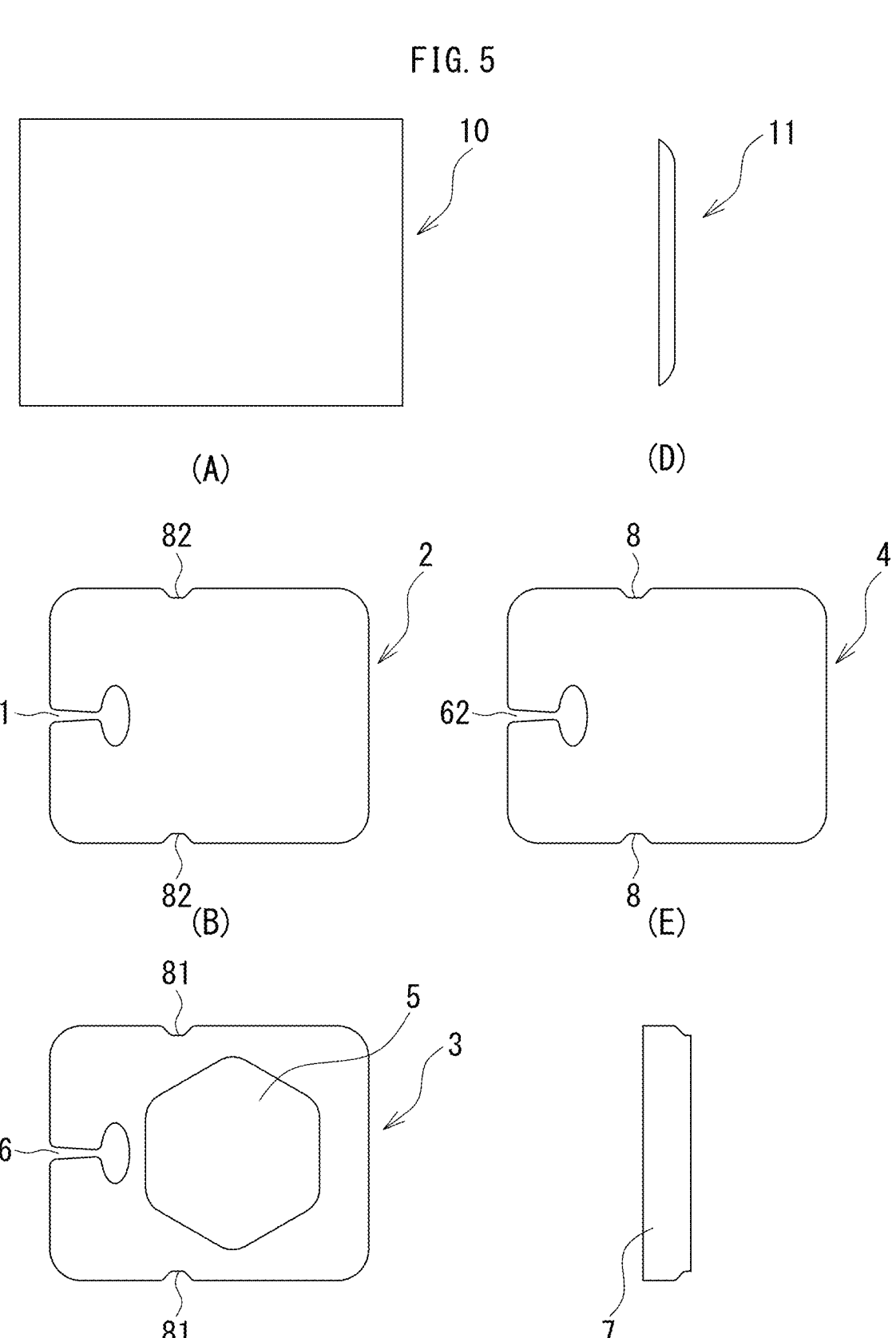
FIG. 5 is plan views of respective laminated layers in the cross-sectional surface of the dressing material for puncture of the present invention illustrated in FIG. 4.

FIG. 3 is a cross-sectional view of a dressing material for puncture including a non-adhesive processed portion (11) described later between the frame sheet (3) and the release liner (4) of the dressing material for puncture illustrated in FIG. 2. FIG. 4 is a cross-sectional view of an exemplary dressing material for puncture of the present invention further including a carrier film (10), which is described later, directly in close contact with the support film (2) of the dressing material for puncture of FIG. 3 on the upper side of the support film. FIG. 5 is plan views of the respective laminated layers in the cross-sectional surface of the dressing material for puncture of the present invention illustrated in FIG. 4.

Due to the non-adhesive processed portion (11) provided, the layer of the adhesive bonding the frame sheet (3) to the release liner (4) is illustrated to be thicker than the layer of the adhesive bonding the support film (2) to the frame sheet (3) in FIG. 3 and FIG. 4. However, it is only for the explanation.

The laminated layers are each described below with reference to FIG. 3 to FIG. 5.
Carrier Film (10)

The carrier film (10) is a film disposed on the upper side of the support film (2) to be in close contact with the support film (2). The carrier film (10) is disposed to avoid direct touch of the ultrasonic jelly with the support film (2). The carrier film (10) is not necessarily disposed.

The carrier film (10) has a function of holding the ultrasonic jelly and removing the whole ultrasonic jelly by the removal of the carrier film after the ultrasound examination. Therefore, the carrier film (10) is not limited insofar as the size and the shapes do not affect the function. While FIG. 5(A) illustrates only an example of the carrier film, the carrier film (10) preferably has a size larger than layers below the carrier film (10) to cover the lower layers.
Support Film (2)

The support film (2) is a film having a function of allowing visually and ultrasonically confirming the holding state of the tip as needed after the dressing material is placed. Then, when the carrier film (10) is not provided, the support film (2) has a function of the carrier film (10). To avoid the direct touch of the ultrasonic jelly with skin, the ultrasonic jelly is applied over the support film (2), and the support film (2) is used to confirm the position of the anatomical structure (for example, the vein) through the support film with a probe. FIG. 5(B) illustrates an exemplary support film (2). A slit portion (61) and a cutout portion (82) are optional structures as described later.
Frame Sheet (3)

The frame sheet (3) mainly has a function of supporting the support film (2), and the ultrasonic transparency is not required. While the frame sheet (3) may be omitted, the frame sheet (3) is preferably provided.
Slit Portion (6, 61, 62)

The frame sheet (3) can be further provided with a keyhole-shaped slit portion (6) at the device placement side of the frame sheet (3) as illustrated in FIG. 5(C). The slit portion (6) penetrates the frame sheet (3) from the front surface to the back surface, and is cut out to expose the puncture device from the dressing material. The keyhole shape is designed to expose the puncture device, such as a needle, punctured to an examination target from the keyhole after the puncture and avoid the direct touch of the exposed puncture device with the body surface using the frame sheet at both sides of the slit portion, thereby reducing skin irritation such as medical device pressure injuries.

FIG. 5(C) illustrates only an example of the keyhole-shaped slit portion (6). In addition to the keyhole, the shape may be one linear or curved slit, a cross-shaped slit, or the like. In the case of a slit, the slit may have a certain degree of width. The shape only needs to allow the puncture device to be exposed from the slit portion, and the shape is preferably a keyhole shape.

The slit portion (6) has a size set depending on a size of the tip of the puncture device to be fixed. Basically, the slit portion (6) has a length of 15% to 25% of a longitudinal length of the dressing material. In the case of the slit portion of the dressing material illustrated in FIG. 5(C), for example, the longitudinal length of the dressing material is 120 mm, and the length of the keyhole-shaped slit portion is 25 mm.

Depending on the usage condition, the frame sheet (3) without the slit portion (6) can be used.

Furthermore, the frame sheet (3) is provided with the observation window (5) as illustrated in FIG. 5(C). The observation window (5) is used to visually and ultrasonically observe the holding state of the tip of the puncture device fixed to the body surface after puncture. While the drawing illustrates the observation window in an approximately hexagonal shape, the shape is not limited thereto, and the shape can be changed as necessary. The observation window (5) can be coupled to the slit portion (6) to be integrated.

The support film (2) and the release liner (4) illustrated in FIGS. 5(B) and 5(E) are disposed to be stacked with the frame sheet (3) interposed therebetween. When the frame sheet (3) is provided with the slit portion (6), the support film (2) and the release liner (4) are also provided with slit portions (61, 62) having shapes similar to the shape of the slit portion (6) of the frame sheet (3). In the dressing material for puncture of the present invention, these slit portions (6, 61, 62) are exactly overlapped.

In practical use, the slit portion (62) of the release liner (4) is not used, and may be omitted, but the slit portion is provided to the release liner as well in some cases in consideration of the production process, the appearance, and the like.

When the frame sheet (3) is not provided with the slit portion (6), it is not necessary to provide the slit portions (61, 62).

Release Liner (4)

In the present invention, the release liner (4) means a seal that is all peeled off at the use of the dressing material and exposes the adhesive (9). As illustrated in FIG. 5(E), the release liner (4) has a shape similar to the shape of the support film (2).

Since a release liner ordinarily used for a tape can be used as the release liner (4), the base material is not limited.

As illustrated in FIG. 3, since the observation window (5) is filled with the adhesive (9), the release liner (4) is bonded to the frame sheet (3) and the support film (2) by the adhesive (9).

Non-Adhesive Processed Portion (11)

Although it is not essential, when the frame sheet (3) is used, an adhesive-deactivating process is performed on a part of the adhesive between the release liner (4) and the frame sheet (3), and the non-adhesive processed portion (11) is provided through this process, and the non-adhesive processed portion (11) functions as a starting point to peel off the release liner (4) (see FIG. 3). When the frame sheet (3) is not used, the adhesive-deactivating process is performed on a part of the adhesive between the release liner (4) and the support film (2), thereby providing the non-adhesive processed portion (11).

The adhesive-deactivating process can be performed by an ordinarily used method. For example, an adhesive-deactivating agent is applied, or a seal is attached, thereby allowing eliminating the adhesiveness.

Examples of the adhesive-deactivating agent include a UV ink. As the UV ink, for example, inks of UV VNL series, inks of UV161 series, and inks of UV VP S series (all manufactured by T&K TOKA Corporation) can be used.

Examples of the seal include polyethylene terephthalate (PET). In this application, the seal is referred to as a non-adhesive seal. An adhesive may be applied over the non-adhesive seal, or does not need to be applied over the non-adhesive seal, and the non-adhesive seal only needs to be attached to the adhesive (9) at the release liner (4) side between the frame sheet (3) and the release liner (4) to form the non-adhesive processed portion (11) (see FIG. 5(D)).

In the use, since the non-adhesive processed portion (11) eliminates the adhesiveness of the adhesive on the frame sheet (3) at the release liner (4) side, the release liner (4) can be easily pinched and smoothly peeled off. Since the non-adhesive processed portion (11) is not adhered to the release liner (4), the non-adhesive processed portion (11) is not peeled off.

As the starting point to peel off the release liner (4), instead of the non-adhesive processed portion (11), although not illustrated, a seal that serves as a tab can be provided to the release liner (4) at the skin side. The seal can be designed to be coupled with a part of the release liner and to have a shape exposed or not exposed from the dressing material. When peeling off the release liner (4), by pinching the tab seal and peeling off the tab seal, the release liner (4) can be peeled off together.

Folded Tape (7)

Although it is not essential, a folded tape (7) that functions as a fold can be further disposed. As illustrated in FIG. 2, the folded tape (7) is disposed at a part of a lower surface of the release liner to partially cover the observation window (5) described below.

The folded tape (7) is located near a puncture site, and the release liner (4) in the opposite side of the device placement side is peeled off up to the folded tape (7) as the fold and folded at first in the use. Considering convenience, basically, the folded tape has a linear side edge in the opposite side of the device placement side, and the folded tape has a simple rectangular shape (FIG. 5(F)). However, the shape of the folded tape is not limited insofar as a purpose of functioning as a fold is achieved. In one embodiment, to easily form the fold, for example, one perforation line or two parallel perforation lines often used for an adhesive tape may be provided to the release liner (4) instead of the folded tape.

Cutout Portion (8, 81, 82)

To easily fold the release liner (4), as illustrated in FIG. 5(E), one cutout portion (8) having a recessed shape can be further provided for each of both side edges extending in a longitudinal direction of the release liner (4). A straight line connecting the two cutout portions in a short side direction overlaps with a side edge of the folded tape (7) in the opposite side of the device placement side.

Furthermore, from an aesthetic merit, cutout portions (81) and cutout portions (82) having shapes similar to those of the support film (2) and the frame sheet (3) can be provided at positions similar to those of the cutout portions (8) of the release liner (4) so as to be exactly overlapped. When the cutout portion (8) is not provided at the release liner (4), it is not necessary to provide the cutout portions (81, 82).

As described above, since the frame sheet (3) mainly functions to support the support film (2), the frame sheet (3) may be omitted when the use of the dressing material for puncture is not affected.

That is, in addition to the dressing material for puncture of the present invention illustrated in FIG. 2, there is a dressing material for puncture without the frame sheet (3) as illustrated in FIG. 6(A) in another embodiment. When the non-adhesive processed portion (11) is necessary, the non-adhesive processed portion (11) is located between the support film (2) and the release liner (4) (FIG. 6(B)).

Similarly, as illustrated in FIG. 6(C), there is an embodiment in which the carrier film (10) that is directly in close contact with the support film is further disposed on the upper side the support film (2) to be bonded illustrated in FIG. 6(A).

Figure 6:
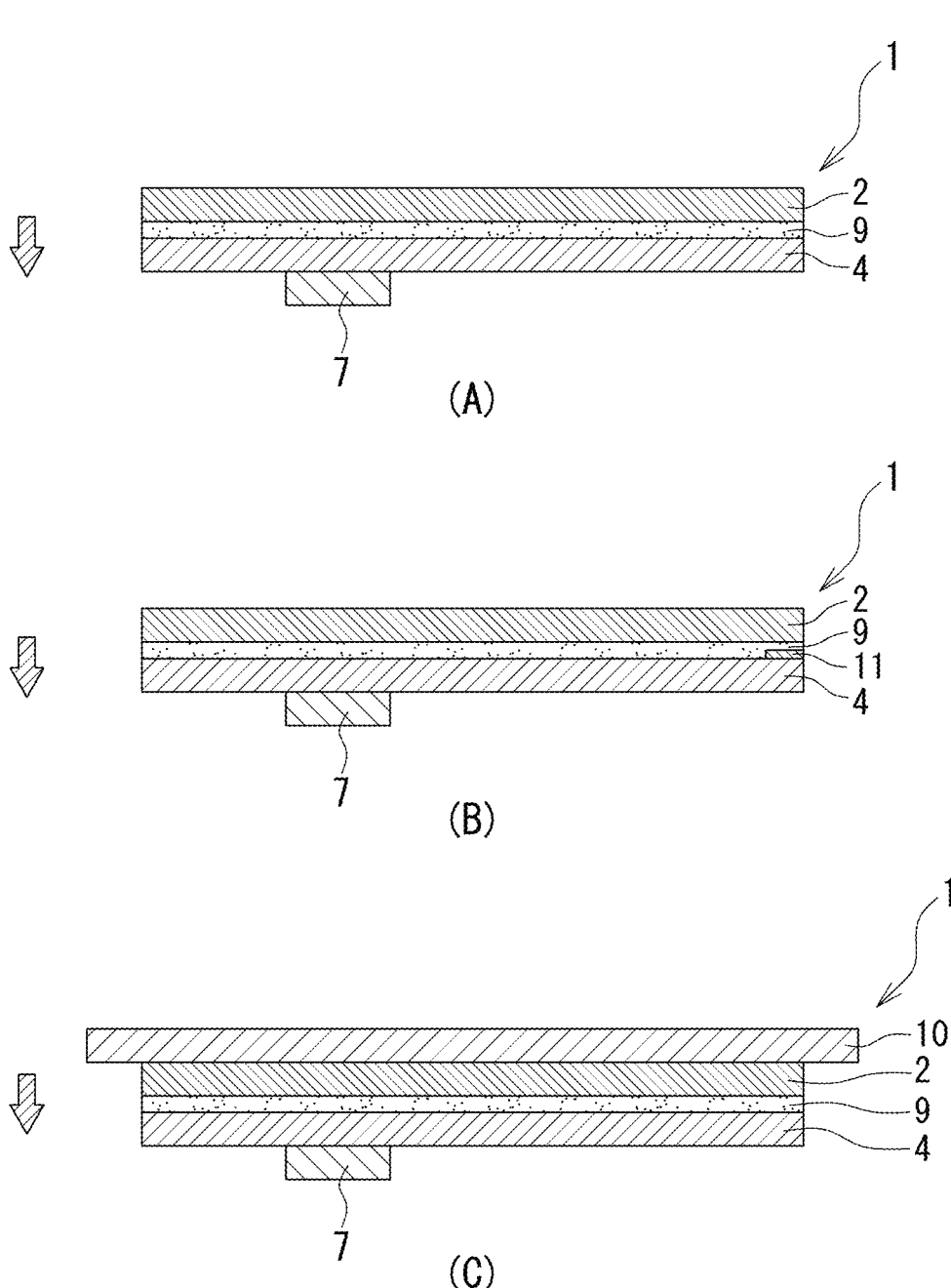
FIG. 6 is a cross-sectional view of a dressing material for puncture of the present invention in one embodiment in which the frame sheet is not provided.

Although not illustrated in the cross-sectional views of the dressing materials of FIG. 6, depending on the usage condition, the slit portions (61, 62) can be provided at the support film (2) and the release liner (4). While the folded tape (7) is disposed in FIGS. 6(A) and 6(B), the folded tape (7) is not essential, and may be omitted. Similarly, while the cutout portion cannot be illustrated in the cross-sectional views, the cutout portion is provided depending on the usage condition.

(Use Method of Dressing Material for Puncture)

A use method of the dressing material for puncture of the present invention will be described below with the dressing material for puncture illustrated in FIG. 4 and FIG. 5 as an example.

Before using the dressing material for puncture of the present invention, first, blood vessel running is confirmed by an ultrasound examination to determine a position to be punctured, echo jelly at the position planned to be punctured is removed, and the position to be punctured is sterilized (body surface may be marked).

Then, a position at which the dressing material for puncture is attached is determined such that the observation window (5) of the dressing material for puncture of the present invention covers the position to be punctured.

Subsequently, the side edge of the release liner (4) in the opposite side of the device placement side is pinched, and the release liner (4) is removed up to the folded tape (7).

The adhesive on the exposed frame sheet (3) and support film (2) is attached to an examination site while avoiding entering of air to the skin (see FIG. 7(A)). When air enters between the ultrasonic device and the skin, since the air obstructs formation of an ultrasonic signal, especially the portion of the observation window (5) that is a scanning area is firmly attached to the skin.

Subsequently, a probe over which the ultrasonic jelly is applied is placed on the carrier film (10) (when the dressing material for puncture without the carrier film illustrated in FIG. 1, FIG. 2, and FIG. 3 is used, the probe over which the ultrasonic jelly is applied is directly placed on the support film (2)).

The anatomical structure is visualized through the carrier film (10) and the support film (2) using the ultrasonic device, and the position to be punctured is confirmed (see FIG. 7(B)).

While watching an ultrasonic video (for example, illustrated in FIG. 8), the position of the anatomical structure (for example, vein) is confirmed, and puncture is performed with the puncture device (12) (see FIG. 7(C)). The puncture device is detected by the ultrasonic device, and the correct placement of the puncture device is obtained.

When the puncture is succeeded, the catheter is placed in the blood vessel, and then the carrier film (10) with the ultrasonic jelly is peeled off (see FIG. 7(D)) (when the dressing material for puncture without the carrier film illustrated in FIG. 1, FIG. 2, and FIG. 3 is used, the ultrasonic jelly attached to the support film is wiped off).

Subsequently, the remaining part of the release liner (4) is fully peeled off (see FIG. 7(E)).

Furthermore, the puncture device (12) is fixed by the frame sheet around the slit portion (6) (see FIG. 7(F)). Direct touch of the puncture device with the skin harms the skin in some cases. At the fixing, by successfully fixing the puncture device to the skin with the slit portion to avoid the direct touch of the puncture device with the skin, such a damage can be avoided.

As illustrated in FIG. 7(F), finally, other than the adhesive, only the support film (2) and the frame sheet (3) are left at the examination site. When the observation window portion of the support film (2) is transparent, the holding state of the tip of the fixed puncture device can be confirmed through the observation window (5).

When the position to be punctured is confirmed with the ultrasonic sound wave, the portion other than the slit portion (6) of the frame sheet (3) serves to fix the dressing material for puncture to the examination target, and the slit portion (6) serves to fix the puncture device (12) to the examination target after the puncture.

As another use method of the dressing material for puncture of the present invention, a step of peeling off the carrier film (10) with the ultrasonic jelly after the end of the puncture may be changed to a step of removing the ultrasonic jelly while leaving the carrier film (10) as it is.

A use method of the dressing material for puncture without the frame sheet (3) is not different from the use method of the dressing material for puncture with the frame sheet (3). Finally, only the adhesive (9) and the support film (2) are left at the examination site.

Figure 7:
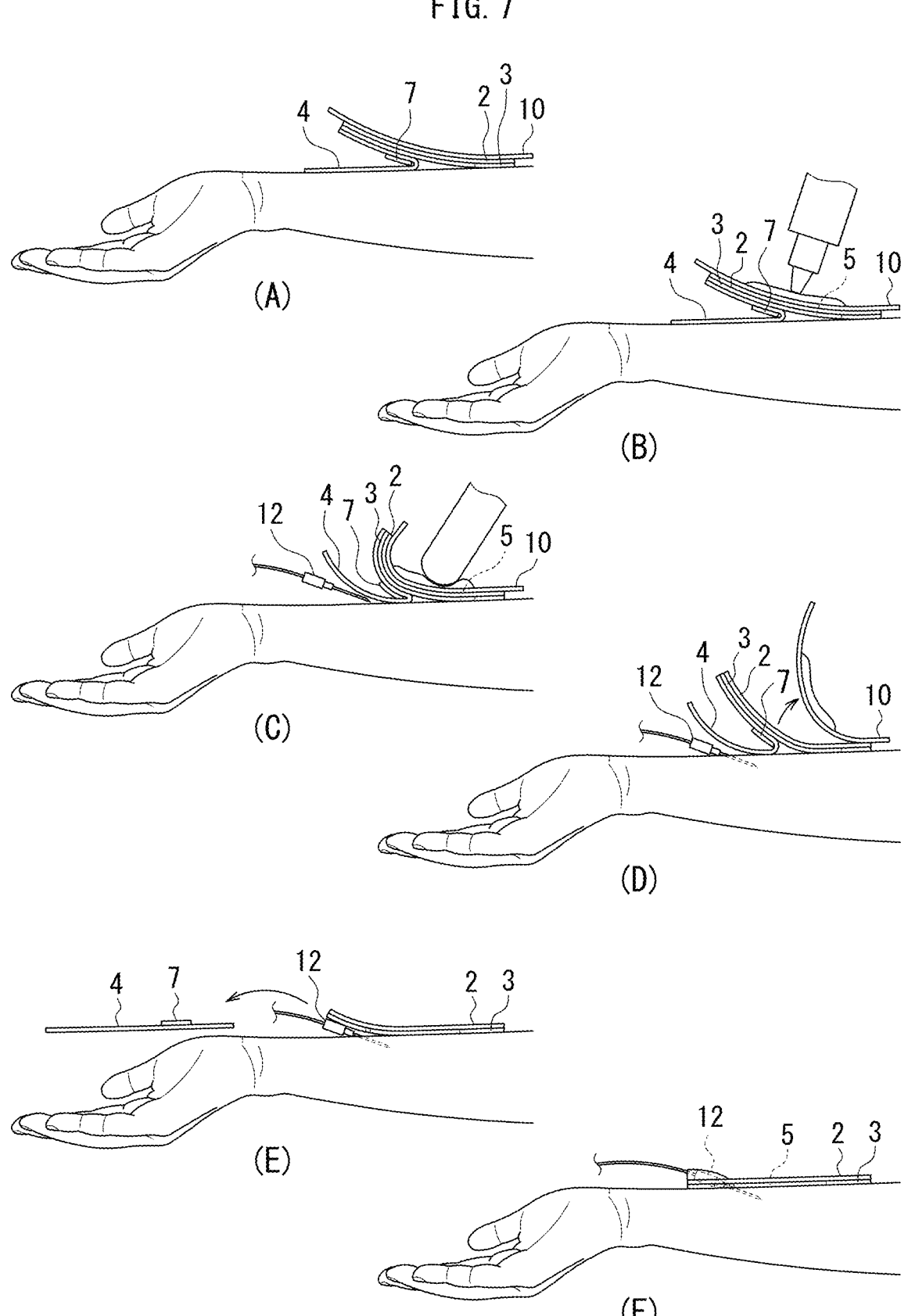
FIG. 7(A) to FIG. 7(F) illustrate an exemplary procedure for suing the dressing material for puncture of the present invention illustrated in FIG. 4 and FIG. 5.

A use method of the dressing material for puncture with one perforation line at the center of the release liner of the present invention is not different from the use method of the dressing material for puncture illustrated in FIG. 7 excluding a step of removing the release liner up to the perforation line of the release liner and attaching the adhesive of the exposed frame sheet and support film to the examination site before puncture, and a step of removing the remaining part of the release liner after the puncture.

A use method of the dressing material for puncture with two perforation lines at the center of the release liner of the present invention is not different from the use method of the dressing material for puncture illustrated in FIG. 7 excluding a step of removing the center portion of the release liner along the two perforation lines and attaching the adhesive of the exposed frame sheet and support film to the examination site before puncture, and a step of removing both side portions of the release liner after the puncture.

In the present invention, in addition to the ultrasonic jelly, touch means similar to the ultrasonic jelly can be used.

(Constituent Materials of Respective Layers of Dressing Material for Puncture)

[Base Material of Carrier Film (10)]

The carrier film (10) has a function of holding the ultrasonic jelly in the ultrasound examination and has a barrier function to avoid the touch of the ultrasonic jelly with the puncture device (12).

It is necessary to use a base material having an ultrasonic transparency for the carrier film (10). Examples of an ordinarily used material include a polyolefin-based material and a polyvinyl alcohol-based material, such as polyethylene (PE), oriented polypropylene (OPP), ethylene-propylene copolymer, ethylene-butene-1 copolymer, ethylene-octene copolymer, ethylene-vinyl acetate copolymer, and ethylene-vinyl alcohol copolymer, an acrylic-based material, such as polymethyl methacrylate, a polyester-based material, such as polyethylene terephthalate (PET) and polybutylene terephthalate, a polyamide-based material, such as nylon 6 and nylon 6,6, various kinds of ionomer-based materials having metal ions, such as zinc and sodium, in the structure, a styrene-based material, such as polystyrene, styrene-isoprene copolymer, and styrene-butadiene copolymer, a polyurethane-based material, a vinyl chloride-based material, a fluorine-based material, and a cellulose-based material, such as acetate and cellophane. The satisfactory ultrasonic transparency is obtained when the above-described materials have a thickness of 10 μm to 80 μm. The thickness is further preferably 10 μm to 60 μm. The thickness is more preferably 10 μm to 40 μm.

[Base Material of Support Film (2)]

Since the support film (2) includes a scanning area for confirming the position to be punctured with the ultrasonic sound wave, the support film (2) obviously has the ultrasonic transparency. Further, since the support film (2) finally needs to be tightly attached to the skin, especially, elasticity, flexibility, and stretchability are required.

Examples of the base material used for the support film (2) include a polyolefin-based material and a polyvinyl alcohol-based material, such as polyethylene (PE), oriented polypropylene (OPP), ethylene-propylene copolymer, ethylene-butene-1 copolymer, ethylene-octene copolymer, ethylene-vinyl acetate copolymer, and ethylene-vinyl alcohol copolymer, an acrylic-based material, such as polymethyl methacrylate, a polyester-based material, such as polyethylene terephthalate (PET) and polybutylene terephthalate, a polyamide-based material, such as nylon 6 and nylon 6,6, various kinds of ionomer-based materials having metal ions, such as zinc and sodium, in the structure, a styrene-based material, such as polystyrene, styrene-isoprene copolymer, and styrene-butadiene copolymer, a polyurethane-based material, such as polyurethane (U), a vinyl chloride-based material, a fluorine-based material, and a cellulose-based material, such as acetate and cellophane.

Basically, insofar as the obtained thickness of the support film (2) is 10 μm to 80 μm, any base material can provide the satisfactory ultrasonic transparency. The thickness of the support film (2) is preferably 10 μm to 40 μm. The thickness of the support film (2) is more preferably 10 μm to 20 μm.

[Base Material of Frame Sheet (3)]

The ultrasonic transparency is not required of the base material used for the frame sheet (3). However, because of the function of fixing to the skin and the function of fixing the puncture device to the examination target, flexibility and elasticity are required. Any material having the flexibility and the elasticity can be used. For example, any material included in the examples of the support film (2) can be used. Since a base material having a certain degree of strength is preferable, a fibrous material can be used. That is, as the base material used for the frame sheet (3), polyurethane nonwoven fabric or polyethylene terephthalate nonwoven fabric is preferable. The thickness is not specifically limited.

[Adhesive]

For the adhesive to bonding the support film (2) and the frame sheet (3) and bonding the frame sheet (3) and the release liner (4), sufficient adhesiveness to the skin surface is obviously required. Further, the ultrasonic transparency is also required, and since the adhesive is in touch with the skin for a long period of time after the end of puncture, the adhesive is required to be less irritating to the skin and have a high moisture permeability to avoid bacterial growth. The adhesive is not specifically limited insofar as the adhesive meets the above-described requirements, an adhesive containing any synthetic resin including acrylic-based, urethane-based, silicone-based, rubber-based, polyvinyl alcohol-based, polyamide-based, and polyvinyl acetate-based synthetic resins can be used. Among them, an acrylic adhesive and a urethane adhesive are especially preferable.

Examples of the acrylic adhesive include a homocopolymer of (meth)acrylic acid alkyl ester monomer, such as butylacrylate, 2-ethylhexyl acrylate, and isononyl acrylate, or a copolymer of a plurality of these monomers, and further, a copolymer of the (meth)acrylic acid alkyl ester monomer and another monomer copolymerizable therewith, such as (meth)acrylic acid, hydroxyalkyl ester of (meth)acrylic acid, vinyl acetate, styrene, vinylpyrrolidone, (meth)acrylamide, and alkoxyalkyl (meth)acrylate. Among them, an acrylic adhesive containing a copolymer, where (meth)acrylic acid alkyl ester is a main component, is more preferable.

Examples of the urethane adhesive include a urethane polymer obtained using polyol and polyisocyanate. From the aspect of skin irritation, the adhesive preferably has a mass ratio (OH/NCO) of polyol or polyurethane polyol having 1 to 3 hydroxyl groups to polyisocyanate or polyurethane prepolymer having 2 to 3 isocyanate groups in a range of from 1.55 to 1.90, more preferably in a range of from 1.60 to 1.85. OH/NCO smaller than the range makes the adherability to the skin for a long period of time poor, and OH/NCO larger than the range easily causes cohesive failure at the peeling off from the skin.

While polyol is not specifically limited, examples of polyol include hydroxy compound, amine compound, carboxylic acid compound, thiol compound, and polyether polyol having a hydroxyl group. Examples of the hydroxy compound include ethylene glycol, diethylene glycol, propylene glycol, dipropylene glycol, tripropylene glycol, 1,3-propanediol, 1,3-butanediol, 1,4-butanediol, 2,3-butanediol, 1,6-hexanediol, 1,9-nonanediol, 2,5-hexanediol, 1,3-cyclohexanediol, 2-methylpentane-2,4-diol, 2,5-dimethyl-2,5-hexanediol, glycerin, trimethylolpropane, hexanetriol, pentaerythritol, diglycerin, sorbitol, sucrose, glucose, 2-naphthol, and bisphenol. Examples of the amine compound include ethylenediamine, 1,3-propylene diamine, 1,4-butylene diamine, and 1,2-butylene diamine. Examples of the carboxylic acid compound include phthalic acid and adipic acid. Examples of the thiol compound include ethanedithiol and butanedithiol. Examples of the polyether polyol having a hydroxyl group include polyether polyol having a molecular weight of 200 or more and 10000 or less.

As polyisocyanate, a compound having at least two isocyanate groups can be used, and is not specifically limited. Examples of the compound include 2,4-tolylene diisocyanate, 2,6-tolylene diisocyanate, 2,4'-diphenylmethane diisocyanate, 4,4'-diphenylmethanediisocyanate, 1,5-naphthalene diisocyanate, tolidine diisocyanate, xylylene diisocyanate, 1,3-phenylene diisocyanate, 1,4-phenylene diisocyanate, lysine diisocyanate, triphenylmethane triisocyanate, tetramethylxylene diisocyanate, 1,6-hexamethylene diisocyanate, 4,4'-dicyclohexylmethane diisocyanate, isophorone diisocyanate, 1,4-cyclohexane diisocyanate, norbornane diisocyanate, lysine ester triisocyanate, 1,6,11-undecane triisocyanate, 1,8-diisocyanate-4-isocyanate methyl octane, 1,3,6-hexamethylene triisocyanate, bicycloheptane triisocyanate, trimethylhexamethylene diisocyanate, isocyanate-containing urethane prepolymer obtained by a reaction of polyol therewith, and a mixture of two or more thereof. Furthermore, a modified product of the above-described isocyanate (modified product containing urethane group, carbodiimide group, allophanate group, urea group, biuret group, isocyanurate group, amide group, imide group, uretonimine group, uretdione group, or oxazolidone group), and a condensation product (referred to as a polynuclear substance in some cases), such as polymethylene polyphenylene polyisocyanate (polymeric MDI), are included.

Furthermore, the adhesive of the dressing material for puncture of the present invention meets requirements on a specific parameter in a dynamic viscoelasticity measurement (measurement temperature: 32° C. (constant), distortion: 0.1%, normal force: 3N, frequency sweep range: 0.01 Hz to 1,000 Hz).

Especially, it was found from the dynamic viscoelasticity measurement at 32° C. that an adhesive preferably has a storage elastic modulus of 15 KPa or less and has a loss tangent (tan δ) of 0.4 or more at an angular frequency of 1 rad/s. Furthermore, it was found from the dynamic viscoelasticity measurement at 32° C. that an adhesive preferably has a storage elastic modulus of 28 KPa or less and has a loss tangent (tan δ) of 0.65 or more at an angular frequency of 1 rad/s.

Further, it was found that the adhesive flows to skin grooves to reduce air entrapment between the support body and he skin, and this provides the satisfactory ultrasonic transparency. Basically, when the adhesive is applied thick, and the application amount is 30 g/m² or more, the satisfactory result of the ultrasonic transparency is obtained. A range of from 30 g/m² to 80 g/m² and a range of from 35 g/m² to 70 g/m² are acceptable in practical use.

The final thickness of the dressing material of the present invention when used, that is, the total thickness of the support film (2) and the adhesive (9) part filling the space of the observation window part is from 47 µm to 120 µm. The total thickness is preferably from 47 µm to 100 µm, and more preferably from 49 µm to 90 µm.

Furthermore, to achieve the storage elastic modulus and obtain the satisfactory ultrasonic transparency, it is effective to add a plasticizer to the adhesive. Examples of the plasticizer include: fatty acid ester containing higher fatty acid having 12 to 16 carbon atoms, such as IPM-R (isopropyl myristate), ethyl laurate, and isopropyl palmitate, and lower monovalent alcohol having 1 to 4 carbon atoms; fatty acid having 8 to 10 carbon atoms; glycols, such as ethylene glycol, diethylene glycol, triethylene glycol, polyethylene glycol, propylene glycol, and polypropylene glycol; oils and fats, such as olive oil, castor oil, squalene, and lanolin; organic solvents, such as ethyl acetate, ethyl alcohol, dimethyldecyl sulfoxide, decyl methyl sulfoxide, dimethylsulfoxide, dimethylformamide, dimethylacetamide, dimethyl laurylamide, dodecylpyrrolidone, isosorbitol, oleyl alcohol, and lauric acid; liquid surfactants; and ethoxylated stearyl alcohol, glycerin ester, isotridecyl myristate, N-methylpyrrolidone, ethyl oleate, oleic acid, diisopropyl adipate, octyl palmitate, 1,3-propanediol, and glycerin.

The adhesive for bonding the support film (2) and the frame sheet (3) and the adhesive for bonding the frame sheet (3) and the release liner (4) may be the similar adhesive, and may be different adhesives. For example, an acrylic adhesive is used for both adhesives. Alternatively, one is a urethane adhesive, and the other is an acrylic adhesive. Furthermore, even when the same acrylic adhesive is used, the same one type may be used, different two types may be used, and different several types may be used in mixture.

[Base Materials of Release Liner (4), Folded Tape (7), and Non-Adhesive Processed Portion (11)]

The base material of the release liner (4) only needs to be a material that can be easily removed from the frame sheet (3) and the support film (2). For example, a polyethylene terephthalate (PET) film is used.

Since the folded tape (7) that functions as a fold only needs to be attached to the release liner (4), the base material of the folded tape (7) is not specifically limited. For example, an oriented polypropylene (OPP) film can be used.

In the case of a seal, as the base material of the non-adhesive processed portion (11), a PET film, a urethane film, or the like can be used.

The carrier film (10) and the support film (2) may be entirely transparent or partially transparent. Furthermore, the frame sheet (3) may be entirely or transparent.

Consequently, when the body surface of the examination site is marked when punctured, an operator who inserts the puncture device can see the mark of the ultrasonic device, can quickly determine the position of the puncture device to the anatomical structure without causing discomfort to the patient, and can accurately insert the puncture device into the anatomical structure. This leads to the improvement of QOL of the patient and the reduction of the burden on medical workers. Additionally, after the puncture, the holding state of the tip of the puncture device can be observed over time.

The dressing material of the present invention preferably has the moisture permeability of 1,000 (g/m²·24 hr) or more. The moisture permeability of 1,000 (g/m²·24 hr) or more reduces stuffiness when attached to the skin, and reduces skin irritancy and itch during the attachment, thus allowing the attachment for a long period of time. The moisture permeability of the patch material is more preferably 1,500 (g/m²·24 hr) or more, and especially preferably 1,800 (g/m²·24 hr) or more. The higher moisture permeability is more preferable, and the upper limit of the preferable moisture permeability is not specifically set. However, the moisture permeability is usually 10,000 (g/m²·24 hr) or less.

(Manufacturing Method of Dressing Material)

Although not limited, as one example, the dressing material of the present invention is manufactured by sequentially laminating the respective layers with the adhesive. First, the adhesive is applied over the skin side of the support film (2), the frame sheet (3) is stacked thereon as necessary, the adhesive is further applied over the frame sheet (3), and the release liner is stacked thereon. Further, as necessary, the carrier film (10) directly in close contact with the opposite surface of the skin side of the support film (2) can be disposed.

EXAMPLES

The following describes the present invention in further detail with examples. However, the present invention is not limited to these examples.

Example 1 Relation Between Base Material Types of Carrier Film (10) and Support Film (2) and Ultrasonic Transparency The carrier film (10) and the support film (2) were prepared by compositions and manufacturing methods in Table 1 below, and Sakamoto model was used. The ultrasonic jelly was placed on the Sakamoto model, and the ultrasonic transparency and a luminance difference were evaluated for each base material.

TABLE 1

| Sample Name | Adhesive Type — | Mass Ratio (OH/NCO) — | Target Amount of Application g/m² | Base Material Type*¹ | Base Material Specification | Base Material Thickness µm | Thickness After Adhesive Application µm | Δ Luminance — | Ultrasonic Transparency Rating |
|---|---|---|---|---|---|---|---|---|---|
| Base Material 1 | Urethane | 1.75 | 40 | PET | PET Film Alone | 12 | 52 | 36.8 | 3 |
| Base Material 2 | Base | | | | PET Film Alone | 27 | 64 | 31.7 | 3 |
| Base Material 3 | | | | | PET Film Alone | 41 | 77 | 27.8 | 3 |
| Base Material 4 | | | | | PET Film Alone | 53 | 93 | 25.7 | 2 |
| Base Material 5 | | | | | PET Film Alone | 79 | 122 | 19.5 | 2 |
| Base Material 6 | | | | PE | PE Film Alone | 46 | 87 | 37.8 | 3 |
| Base Material 7 | | | | | PE Film Alone | 63 | 102 | 34.6 | 3 |

TABLE 1-continued

| Sample Name | Adhesive Type — | Mass Ratio (OH/NCO) — | Target Amount of Application g/m$^2$ | Base Material Type*[1] | Base Material Specification | Base Material Thickness μm | Thickness After Adhesive Application μm | Δ Luminance — | Ultrasonic Transparency Rating |
|---|---|---|---|---|---|---|---|---|---|
| Base Material 8 | | | | U | U Film Alone | 18 | 56 | 36.5 | 3 |
| Base Material 9 | | | | OPP + U | Laminated Layer of OPP Film and U Film | 58 | 100 | 34.2 | 3 |

*[1]PET (polyethylene terephthalate), PE (polyethylene), U (polyurethane), OPP (oriented polypropylene)

In Table 1, the similar adhesive was used. A urethane adhesive having a mass ratio (OH/NCO) of polyol to iso-cyanate of 1.75 was applied over one surfaces of base materials having indicated thicknesses by indicated appli-cation amounts (g/m$^2$).

PET, PE, and U indicated in columns of the base material are samples in which the adhesives were applied over the respective base materials, and the samples each simulate the carrier film or the support film alone. OPP+U (laminated layer of oriented polypropylene film and polyurethane film) indicated in the column of the base material is a sample in which a carrier film of oriented polypropylene having the thickness of 40 μm was brought in close contact with a support film of polyurethane having both surfaces over which the adhesive was applied and having the thickness of 20 μm. The sample actually simulates the use of the dressing material for puncture having the carrier film.

(Evaluation of Luminance on Sakamoto Model)

Figure 9:
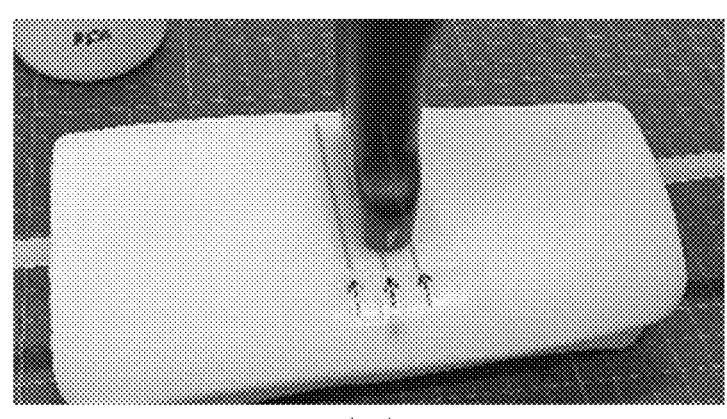
FIG. 9 is photographs illustrating an evaluation method of luminance on artificial arm Sakamoto model.
Figure 9:
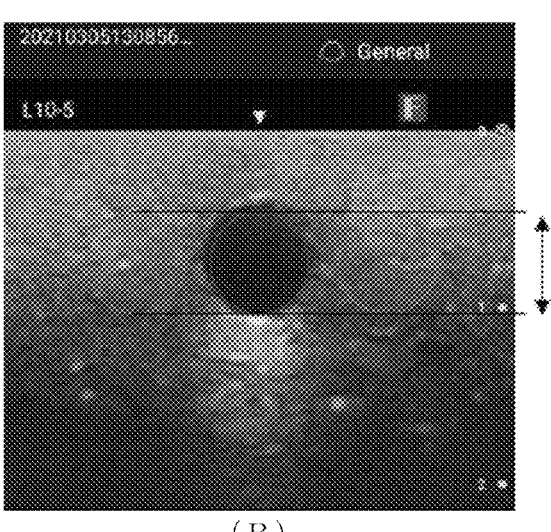

For each of the samples of Table 1, the luminance was evaluated using Sakamoto model. In the measurement, to suppress an influence of an elasticity change of a medium due to temperature change on the luminance, the measure-ment was performed in a test room of 23° C./50% RH. FIG. 9 is photographs indicating an evaluation method of the luminance on an artificial arm Sakamoto model.

Implementation Procedure

1. The samples were left at room temperature of the test room, and a pad portion of echo guide PICC trainer (SAKAMOTO MODEL CORPORATION) in which the temperature was adjusted was provided for the test. Sakamoto model (https://www.sakamoto-model.co.jp/product/echo/m196/index.html#item_discription)
2. As a simulation of blood, distilled water was filled in a hole (blood vessel portion) passing through the pad portion.
3. Each of the samples in a size of about 50×40 mm was attached to the pad surface, and the ultrasonic jelly was applied.
4. A probe (FWL L10-5 linear probe) of wireless ultra-sound diagnostic imaging device iViz air linear (FUJI-FILM Medical Co., Ltd.) was lightly pressed on the sample to obtain ultrasonic images of the blood vessel.
5. The obtained ultrasonic images were analyzed with image analysis software ImageJ (NIH, the United States of America), and a difference of the luminance between the inside of the blood vessel (pad blood vessel portion (circle in the center of FIG. 9(B)) and the outside of the blood vessel (pad substance portion (circles in both sides of FIG. 9(B)) was obtained.

For each of the tape layer samples different in base material type, images were taken at three positions at intervals of about 10 mm, and an average value of luminance difference (Δ luminance) between the respective positions was used as a measurement value (n=3, triplication). The larger the luminance difference is, the easier the blood vessel can be confirmed, and the more satisfactory the ultrasonic transparency is. (Reference: example of using Image J for ultrasonic image analysis (Tomoya Nakagawa, et al. Quality control of sector probe with self-produced phantom in ultrasonography, Journal of analytical bio-science Vol. 42 No. 2 (2019).))

It is seen from the samples of Table 1 that in the case of the base materials of the same type, the thicker the base material is, the more reduced the luminance difference is.

(Evaluation at Human Skin)

For the samples of Table 1, to examine whether or not an ultrasonic image that allows puncture is obtained, the samples were actually attached to human skin, and the ultrasonic transparency was evaluated for ultrasonic images of a cutaneous vein of a forearm according to criteria in Table 2. Ultrasonic transparency ratings of FIGS. 8(A) to 8(E) are the ratings of 0 to 4, respectively according to the evaluation criteria of Table 2. Since the rating of 2 or more allows puncture, the rating 2 is set to a threshold.

When confirming the ultrasonic image, to suppress an influence of an elasticity change of a medium due to temperature change on the ultrasonic transparency, the con-firmation was performed in a test room of 23° C./50% RH.

Implementation Procedure

1. To easily observe the blood vessel, an upper arm of a subject (30s, male) was compressed to a vascularize.
2. Running of the cutaneous vein at the inside of the forearm was observed, and each sample (carrier film (10) (when provided)+support film (2)) having the size of about 30×30 mm was attached to the skin above the blood vessel and lightly press-bonded. The observation was performed near the center of the longitudinal length of the forearm.
3. Immediately, the ultrasonic jelly was applied over the sample.
4. A probe (FWL L10-5 linear probe) of wireless ultra-sound diagnostic imaging device iViz air linear (FUJI-FILM Medical Co., Ltd.) was lightly pressed on the sample to obtain ultrasonic images of the blood vessel (n=1).
5. The obtained ultrasonic images were checked by the rating criteria of Table 2, ease of blood vessel obser-vation (contrast inside and outside the blood vessel and clearness of the blood vessel wall) was compared and rated.

TABLE 2

Ultrasonic Transparency Rating Criteria

Figure 8:
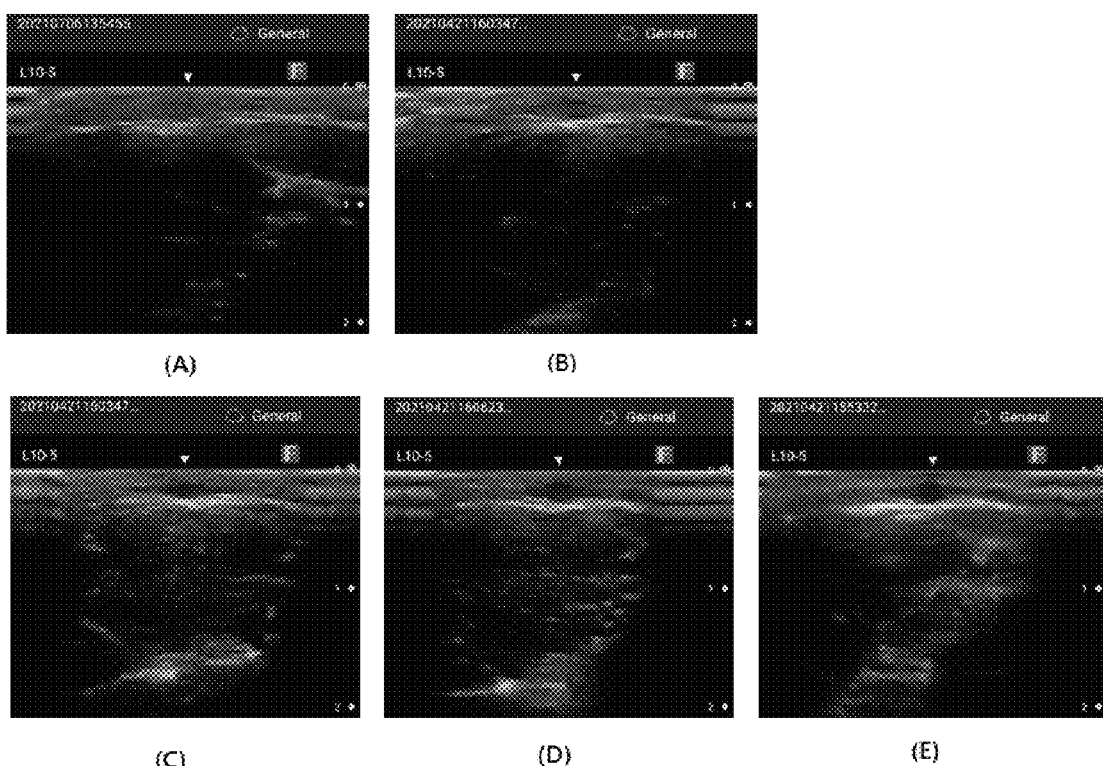
FIG. 8 is ultrasonic images of an inner forearm median vein. White arrows in the images indicate body surface immediately above the vein.

| Rating | | Explanation | FIG. 8 |
|---|---|---|---|
| 0 | Unpuncturable | Blood vessel does not appear at all. | (A) |
| 1 | | Blood vessel appears black, but inside of blood vessel appears white and cloudy. | (B) |
| 2 | Puncturable | Inside of blood vessel appears black, but boundary between inside and outside of blood vessel (blood vessel wall) is slightly blurred. | (C) |

TABLE 2-continued

| | Ultrasonic Transparency Rating Criteria | |
|---|---|---|
| Rating | Explanation | FIG. 8 |
| 3 | Inside of blood vessel appears black, and boundary between inside and outside of blood vessel (blood vessel wall) appears white and clearly. | (D) |
| 4 | Clear blood vessel image is obtained similarly to the case where only ultrasonic jelly is used. | (E) |

It is seen from the samples of Table 1 that in the case of the base materials of the same type, the thicker the base material is, the more reduced the rating of the ultrasonic transparency is.

Since the base materials are different from the human skin and the ultrasonic jelly in elasticity, the ultrasonic transparency is reduced. This effect is more remarkable when the thickness of the base material is increased. From Table 1, while the luminance difference is reduced in the thicker base material in the case of the base materials of the same type, the thicknesses of the base materials in this validation all obtained the satisfactory rating of the ultrasonic transparency.

Consequently, when each of the carrier film (10) and the support film (2) has the thickness of 10 µm or more and 80 µm or less, the satisfactory ultrasonic transparency is obtained. Within the range, there is almost no difference due to the base material.

Example 2 Relation Between Adhesive Softness and Ultrasonic Transparency

Adhesive compositions of acrylic adhesives were produced with compositions of Table 3 to Table 5 below, and a holding force to synthetic paper and a dynamic viscoelasticity at temperature of 32° C. were measured. Then, adhesive compositions of urethane adhesives were produced with compositions of Table 6 below, and a holding force to synthetic paper and a dynamic viscoelasticity at temperature of 32° C. were measured.

Furthermore, the adhesives having the compositions of Table 3 and Table 6 were applied over a material including the OPP carrier film (10) of 40 µm and the urethane support film of 20 µm. These samples were attached to the human skin, the ultrasonic jelly was placed, and the ultrasonic sound wave was applied, thus evaluating the ultrasonic transparency of the ultrasonic images according to the criteria of Table 2.

(Measurement of Holding Force to Synthetic Paper)

As a specific measurement method, a test piece having a width of 12 mm and a length of 20 mm lined with carton tape No. 660 (manufactured by Nichiban Co., Ltd.) was attached to a synthetic paper (manufactured by Yupo Corporation). A rubber roller having a mass of about 2 kg was reciprocated once at a speed of about 300 mm/min for press-bonding, and allowed to stand for 20 minutes to 40 minutes. The test piece and the synthetic paper were vertically fixed, and a weight having a mass of 200 g was hung from one end of the test piece. A length of shifting of the test piece after 60 minutes was read in a unit of 0.1 mm using a scale loupe, and used as a measurement value. The measurement was performed three times, and an average value was obtained as the result.

(Measurement of Dynamic Viscoelasticity at 32° C.)

As a specific measurement method, each of the adhesives were dried to prepare a sheet-shaped test piece having a thickness of about 1 mm. The dynamic viscoelasticity of the test piece was measured using MCR301 (manufactured by Anton Paar GmbH) under conditions of measurement temperature: 32° C. (constant), distortion: 0.1%, normal force: 3N, frequency sweep range: 0.01 Hz to 1,000 Hz (s$^{-1}$). The measurement was performed twice for each test piece, and an average value was obtained as the result.

TABLE 3

| | | Per Hundred Resin (phr) *1 | | | | Target Amount of Application | Holding Force to Synthetic Paper | Storage Elastic Modulus at Angular Frequency of 1 rad/s (G') | Loss Tangent at Angular Frequency of 1 rad/s (tanδ) | Ultrasonic Transparency |
|---|---|---|---|---|---|---|---|---|---|---|
| Sample Name | Adhesive Type | INA | AA | tetrad-X | IPM-R | g/m$^2$ | mm | Pa | — | Rating |
| Acrylic Base 1-1 | Acrylic Base 1 | 96 | 4 | 0.08 | 0 | 42 | 0.1 | 15300 | 0.346 | 0 |
| Acrylic Base 1-2 | | | | | | 35 | 0.1 | | | 1 |
| Acrylic Base 1-3 | | | | 0.05 | | | 0.2 | 14400 | 0.432 | 2 |
| Acrylic Base 1-4 | | | | 0.04 | | | 0.4 | 14350 | 0.445 | 2 |
| Acrylic Base 1-5 | | | | 0.02 | | | 0.7 | 11300 | 0.476 | 3 |
| Acrylic Base 1-6 | | | | 0.05 | 15 | | 0.3 | 5360 | 0.494 | 2 |
| Acrylic Base 1-7 | | | | 0.05 | 30 | | 0.4 | 3540 | 0.576 | 3 |

*1: INA (isononyl acrylate), AA (acrylic acid), IPM-R (isopropyl myristate)

TABLE 4

| | | Per Hundred Resin (phr) *1 | | | | Target Amount of Application | Holding Force to Synthetic Paper | Storage Elastic Modulus at Angular Frequency of 1 rad/s (G') | Loss Tangent at Angular Frequency of 1 rad/s (tanδ) | Ultrasonic Transparency |
|---|---|---|---|---|---|---|---|---|---|---|
| Sample Name | Adhesive Type | 2EHA | Vac | AA | tetrad-X | g/m$^2$ | mm | Pa | — | Rating |
| Acrylic Base 2-1 | Acrylic Base 2 | 85 | 11 | 4 | 0.10 | 42 | 0.2 | 19450 | 0.595 | 1 |
| Acrylic Base 2-2 | | | | | | 35 | 0.1 | | | 1 |
| Acrylic Base 2-3 | | | | | 0.08 | | 0.1 | 27250 | 0.648 | 1 |
| Acrylic Base 2-4 | | | | | 0.06 | | 0.2 | 27750 | 0.667 | 2 |

TABLE 4-continued

| Sample Name | Adhesive Type | Per Hundred Resin (phr) *1 | | | | Target Amount of Application g/m² | Holding Force to Synthetic Paper mm | Storage Elastic Modulus at Angular Frequency of 1 rad/s (G') Pa | Loss Tangent at Angular Frequency of 1 rad/s (tanδ) — | Ultrasonic Transparency Rating |
|---|---|---|---|---|---|---|---|---|---|---|
| | | 2EHA | Vac | AA | tetrad-X | | | | | |
| Acrylic Base 2-5 | | | | | 0.05 | | 0.4 | 27550 | 0.678 | 3 |
| Acrylic Base 2-6 | | | | | 0.03 | | 0.9 | 27350 | 0.698 | 3 |

*1: 2EHA (2-ethylhexyl acrylate), AA (acrylic acid), Vac (vinyl acetate)

TABLE 5

| Sample Name | Adhesive Type | Per Hundred Resin (phr) *1 | | | | Target Amount of Application g/m² | Holding Force to Synthetic Paper mm | Storage Elastic Modulus at Angular Frequency of 1 rad/s (G') Pa | Loss Tangent at Angular Frequency of 1 rad/s (tanδ) — | Ultrasonic Transparency Rating |
|---|---|---|---|---|---|---|---|---|---|---|
| | | INA | 2MTA | AA | tetrad-X | | | | | |
| Acrylic Base 3-1 | Acrylic Base 3 | 68 | 30 | 2 | 0.06 | 42 | 0.0 | 18150 | 0.381 | 0 |
| Acrylic Base 3-2 | | | | | | 35 | 0.0 | | | 0 |
| Acrylic Base 3-3 | | | | | 0.04 | | 0.2 | 12905 | 0.426 | 2 |
| Acrylic Base 3-4 | | | | | 0.03 | | 0.4 | 11015 | 0.445 | 3 |
| Acrylic Base 3-5 | | | | | 0.02 | | 0.7 | 8530 | 0.451 | 3 |

*1: INA (isononyl acrylate), AA (acrylic acid), 2MTA (methoxyethyl acrylate)

TABLE 6

| Sample Name | Adhesive Type | Mass Ratio (OH/NCO) | Target Amount of Application g/m² | Holding Force to Synthetic Paper mm | Storage Elastic Modulus at Angular Frequency of 1 rad/s (G') Pa | Loss Tangent at Angular Frequency of 1 rad/s (tanδ) — | Ultrasonic Transparency Rating |
|---|---|---|---|---|---|---|---|
| Urethane Base 1 | Urethane Base | 1.75 | 42 | 0.8 | 5555 | 0.637 | 3 |
| Urethane Base 2 | | 1.70 | | 0.4 | 5975 | 0.620 | 3 |
| Urethane Base 3 | | 1.65 | | 0.6 | 7995 | 0.495 | 3 |
| Urethane Base 4 | | 1.60 | | 0.3 | 8745 | 0.462 | 3 |
| Urethane Base 5 | | 1.55 | | 0.2 | 13000 | 0.408 | 2 |
| Urethane Base 6 | | 1.45 | | 0.1 | 17750 | 0.320 | 1 |

Since the small measurement value of the holding force to synthetic paper (hard adhesive) causes the adhesive to have difficulty in flowing to skin grooves, the ultrasonic transparency decreases. The threshold is the rating 2, therefore, the adhesive having the holding force to synthetic paper of 0.2 to 0.4 mm or more is soft and provides the satisfactory ultrasonic transparency.

When the storage elastic modulus at the angular frequency of 1 rad/s obtained by the dynamic viscoelasticity measurement at 32° C. is 15 KPa or less, the satisfactory ultrasonic transparency is obtained.

By adding the plasticizer IPM-R to the combination of the acrylic base 1-3, the ultrasonic transparency was improved (acrylic base 1-6, acrylic base 1-7).

Example 3 Relation Between Application Thickness of Adhesive and Ultrasonic Transparency, Moisture Permeability The same urethane adhesive (OH/NCO=1.75) was applied over a material including the OPP carrier film (10) of 40 μm and the urethane support film of 20 μm, and the relation between the different adhesive application thicknesses indicated in Table 7 and the ultrasonic transparency, the moisture permeability. In this example, it is assumed to use the dressing material without the frame sheet, and the measurement is performed. When the dressing material with the frame sheet is used, the thickness of the adhesive part corresponds to the thickness of the adhesive part filling the space of the observation window. As a comparable example, a conventional product ULTRADRAPE™ (manufactured by Parker Laboratories Inc.) was used.

(Moisture Permeability Measurement)

In the present invention, the measurement of the moisture permeability was performed at the temperature of 40° C. and the relative humidity of 90% according to calcium chloride method described in Japanese Industrial Standard L1099. That is, the temperature was adjusted to 40° C. and the relative humidity was adjusted to 90% at one surface side of the patch material, a moisture absorbent, such as calcium chloride, was placed at the other surface side to absorb water content that has passed through the patch material, and the weight change amount of the moisture absorbent was calculated by conversion into a value per 24 hours and square meter.

TABLE 7

| Sample Name | Adhesive Type | Mass Ratio (OH/NCO) | Application Amount g/m² | Total Thickness*¹ μm | Holding Force to Synthetic Paper mm | Moisture Permeability*² g/m² · 24 hr | Ultrasonic Transparency*³ Rating |
|---|---|---|---|---|---|---|---|
| Application Amount 1 | Urethane Base | 1.75 | 7.0 | 21 | 0.2 | 2606 | 0 |
| Application Amount 2 | | | 8.3 | 23 | 0.2 | 2453 | 0 |
| Application Amount 3 | | | 10 | 27 | 0.2 | 2408 | 1 |
| Application Amount 4 | | | 15 | 34 | 0.2 | 2307 | 1 |
| Application Amount 5 | | | 25 | 43 | 0.2 | 2108 | 1 |
| Application Amount 6 | | | 32 | 49 | 0.2 | 2059 | 2 |
| Application Amount 7 | | | 37 | 52 | 0.3 | 2006 | 3 |
| Application Amount 8 | | | 40 | 59 | 0.3 | 1993 | 3 |
| Application Amount 9 | | | 45 | 64 | 0.3 | 1856 | 3 |
| Application Amount 10 | | | 52 | 67 | 0.3 | 1846 | 3 |
| Application Amount 11 | | | 55 | 71 | 0.3 | 1826 | 4 |
| Application Amount 12 | | | 61 | 75 | 0.4 | 1763 | 4 |
| Application Amount 13 | | | 67 | 80 | 0.4 | 1734 | 4 |
| Application Amount 14 | | | 68 | 85 | 0.4 | 1730 | 4 |
| Comparative Example | ULTRADRAPE ®*⁴ | | — | 42 | 0.1 | 461 | 1 |

*¹Total thickness was measured excluding carrier film (thickness about 40 μm).
*²Moisture permeable cup with effective transmission area of 60 mmφ × 1 hole was used for measurement in examples, and moisture permeable cup with effective transmission area of 15 mmφ × 4 holes was used for measurement in comparative example.
*³Ultrasonic transparency was evaluated from above carrier film (thickness about 40 μm).
*⁴Measurement was performed using part at which nonwoven fabric was not attached.

In Table 7, the total thickness is a total thickness of a part excluding the carrier film, that is, a total thickness of the support film and the adhesive applied over the support film.

From the ratings of Table 7, in the case of the urethane adhesive (OH/NCO=1.75), when the application thickness of the adhesive is increased, air entrapment between the tape and the skin due to the adhesive flowing to skin grooves is reduced. Therefore, the satisfactory ultrasonic transparency was obtained. In a conventional product of the comparative example, the blood vessel was hazed white inside, and the blood vessel wall was unclear. Therefore, the ultrasonic transparency was the rating 1 at which the puncture cannot be performed.

To obtain the satisfactory ultrasonic transparency of the rating 2 or more, the application amount may be 30 g/m² or more. Even when the thickness is larger than this, the ultrasonic transparency is approximately the same. For example, even the application amount of 70 g/m² or 80 g/m² exhibited the satisfactory ultrasonic transparency.

It was confirmed that the moisture permeability was considerably improved compared with the conventional product.

The examples described above are for further describing the present invention, and does not limit the scope of the protection of the present invention. Obviously, those skilled in the art can modify and adjust the contents of the present invention in other aspects based on the contents of the present invention without exceeding the scope of the protection of the present invention.

DESCRIPTION OF REFERENCE SIGNS

1 Dressing material for puncture
2 Support film
3 Frame sheet
4 Release liner
5 Observation window
6, 61, 62 Slit portion
7 Folded tape
8, 81, 82 Cutout portion
9 Adhesive
10 Carrier film
11 Non-adhesive processed portion
12 Puncture device

The invention claimed is:

1. A dressing material for puncture, comprising:
a support film having an ultrasonic transparency;
a frame sheet including an observation window to observe a holding state of a tip of a puncture device fixed to a body surface; and
a release liner, wherein
the support film, the frame sheet, and the release liner are laminated from an upper side in this order,
an adhesive is used to bond the support film and the frame sheet, and bond the frame sheet and the release liner,
the support film is a film base material having a thickness of from 10 μm to 80 μm, and
the adhesive has a mass per unit area of from 30 g/m² to 80 g/m²;
wherein the adhesive that bonds the support film and the frame sheet has a storage elastic modulus of 15 KPa or less and a loss tangent (tan δ) of 0.4 or more at an angular frequency of 1 rad/s obtained by a dynamic viscoelasticity measurement at 32° C.

2. The dressing material for puncture according to claim 1, wherein
the adhesive that bonds the support film and the frame sheet is an acrylic adhesive or a urethane adhesive containing a copolymer where (meth)acrylic acid alkyl ester is a main component.

3. The dressing material for puncture according to claim 1, wherein
a total thickness of the support film and an adhesive part filling a space of the observation window is from 47 μm to 120 μm.

4. The dressing material for puncture according to claim 1, wherein
the frame sheet further includes a slit portion to expose the puncture device.

5. The dressing material for puncture according to claim 1, further comprising:
a folded tape coupled with the release liner.

6. The dressing material for puncture according to claim 5, wherein
the folded tape is provided to be coupled with the release liner at a part of a lower surface of the release liner to partially cover the observation window.

7. The dressing material for puncture according to claim 5, wherein the release liner is provided with one cutout portion at each of both edges of the release liner in a longitudinal direction, and a side edge of the folded tape in an opposite side of a device placement side overlaps with a straight line connecting the two cutout portions in a short side direction.

8. The dressing material for puncture according to claim 1, further comprising:

a non-adhesive processed portion between the frame sheet and the release liner to avoid bonding the frame sheet and the release liner.

9. The dressing material for puncture according to claim 1, further comprising:

a carrier film directly in close contact with the support film, the carrier film being on an upper side of the support film, wherein the carrier film has a thickness of from 10 μm to 80 μm.

10. A dressing material for puncture, comprising:

a support film having an ultrasonic transparency;

a frame sheet including an observation window to observe a holding state of a tip of a puncture device fixed to a body surface; and a release liner, wherein the support film, the frame sheet, and the release liner are laminated from an upper side in this order, an adhesive is used to bond the support film and the frame sheet, and bond the frame sheet and the release liner, the support film is a film base material having a thickness of from 10 μm to 80 μm, and the adhesive has a mass per unit area of from 30 g/m$^2$ to 80 g/m$^2$;

wherein the adhesive that bonds the support film and the frame sheet has a storage elastic modulus of 28 KPa or less and a loss tangent (tan δ) of 0.65 or more at an angular frequency of 1 rad/s obtained by a dynamic viscoelasticity measurement at 32° C.

11. The dressing material for puncture according to claim 10, wherein the adhesive that bonds the support film and the frame sheet is an acrylic adhesive or a urethane adhesive containing a copolymer where (meth)acrylic acid alkyl ester is a main component.

12. The dressing material for puncture according to claim 10, wherein a total thickness of the support film and an adhesive part filling a space of the observation window is from 47 μm to 120 μm.

13. The dressing material for puncture according to claim 10, wherein the frame sheet further includes a slit portion to expose the puncture device.

14. The dressing material for puncture according to claim 10, further comprising:

a folded tape coupled with the release liner.

15. The dressing material for puncture according to claim 14, wherein the folded tape is provided to be coupled with the release liner at a part of a lower surface of the release liner to partially cover the observation window.

16. The dressing material for puncture according to claim 14, wherein the release liner is provided with one cutout portion at each of both edges of the release liner in a longitudinal direction, and a side edge of the folded tape in an opposite side of a device placement side overlaps with a straight line connecting the two cutout portions in a short side direction.

17. The dressing material for puncture according to claim 10, further comprising:

a non-adhesive processed portion between the frame sheet and the release liner to avoid bonding the frame sheet and the release liner.

18. The dressing material for puncture according to claim 10, further comprising:

a carrier film directly in close contact with the support film, the carrier film being on an upper side of the support film, wherein the carrier film has a thickness of from 10 μm to 80 μm.

* * * * *